US009028780B2

(12) United States Patent
Auclair et al.

(10) Patent No.: US 9,028,780 B2
(45) Date of Patent: May 12, 2015

(54) COMPOUND SAMPLE NEEDLE FOR LIQUID CHROMATOGRAPH

(75) Inventors: John Auclair, Seekonk, MA (US); James E. Usowicz, Webster, MA (US); Tony A. Lin, Ashland, MA (US); Marc Lemelin, Douglas, MA (US); Robert A. Jencks, Mendon, MA (US); Kenneth R. Plant, Leominster, MA (US)

(73) Assignee: Waters Technologies Corporation, Milford, MA (US)

( * ) Notice: Subject to any disclaimer, the term of this patent is extended or adjusted under 35 U.S.C. 154(b) by 489 days.

(21) Appl. No.: 13/519,687

(22) PCT Filed: Jan. 11, 2011

(86) PCT No.: PCT/US2011/020728
§ 371 (c)(1),
(2), (4) Date: Aug. 27, 2012

(87) PCT Pub. No.: WO2011/085338
PCT Pub. Date: Jul. 14, 2011

(65) Prior Publication Data
US 2012/0328486 A1     Dec. 27, 2012

Related U.S. Application Data

(60) Provisional application No. 61/293,851, filed on Jan. 11, 2010.

(51) Int. Cl.
*G01N 1/10*      (2006.01)
*G01N 30/18*     (2006.01)
(Continued)

(52) U.S. Cl.
CPC ........... *G01N 30/18* (2013.01); *B01L 2200/026* (2013.01); *G01N 1/10* (2013.01);
(Continued)

(58) Field of Classification Search
CPC ... B01L 3/561; B01L 3/563; B01L 2200/026; G01N 1/10
USPC .......................................................... 422/546
See application file for complete search history.

(56) References Cited

U.S. PATENT DOCUMENTS 3,203,455 A * 8/1965 Horabin ......................... 141/329
5,249,610 A * 10/1993 Cassou et al. .................. 141/130
(Continued)

FOREIGN PATENT DOCUMENTS

DE    202007013096 U1    3/2009
EP        0636882 A1     2/1995

OTHER PUBLICATIONS

International Search Report and Written Opinion in counterpart international application No. PCT/US2011/020728, mailed Mar. 7, 2011; 6 pages.
Extended European Search Report in related European patent application No. 11732292.5, mailed on Nov. 27, 2014; 6 pages.

*Primary Examiner* — Jan Ludlow
(74) *Attorney, Agent, or Firm* — Schmeiser, Olsen + Watts LLP

(57) ABSTRACT

Described is a compound sample needle for a liquid chromatography system. In one embodiment, the compound sample needle includes a rigid needle having a coupling end with a face and a counterbore. The compound sample needle also includes a flexible tubing having an outer surface and a coupling end disposed in the counterbore of the rigid needle. The coupling end of the flexible tubing has a face adjacent to a base of the counterbore. The coupling ends of the rigid needle and flexible tubing are secured to each other by a weld formed along a circumference of the outer surface and the face of the rigid needle. A rigid sleeve protects the welded joint. The compound sample needle is suitable for injection into the high pressure mobile phase of ultra performance liquid chromatography systems.

5 Claims, 4 Drawing Sheets

(51) Int. Cl.
*B01L 3/00* (2006.01)
*G01N 30/36* (2006.01)
*G01N 30/24* (2006.01)
*G01N 30/60* (2006.01)

(52) U.S. Cl.
CPC ............... *B01L 3/561* (2013.01); *B01L 3/563* (2013.01); *G01N 30/36* (2013.01); *G01N 30/24* (2013.01); *G01N 30/6039* (2013.01)

(56) References Cited

U.S. PATENT DOCUMENTS

| | | |
|---|---|---|
| 5,938,919 A | 8/1999 | Najafabadi |
| 2008/0172023 A1 | 7/2008 | Thompson et al. |
| 2010/0312194 A1 | 12/2010 | Leckebusch |

* cited by examiner

COMPOUND SAMPLE NEEDLE FOR LIQUID CHROMATOGRAPH

RELATED APPLICATION

This application claims the benefit of the earlier filing date of U.S. Provisional Patent Application Ser. No. 61/293,851, filed Jan. 11, 2010 and titled "Compound Sample Needle for Liquid Chromatography," the entirety of which is incorporated herein by reference.

FIELD OF THE INVENTION

The invention relates generally to liquid chromatography systems. More particularly, the invention relates to a compound sample needle that can be used in a high pressure mobile phase liquid chromatography applications.

BACKGROUND

Ultra performance liquid chromatography (UPLC) systems include a sample compartment that holds one or more sample trays. Each tray has a number of sample vials or wells containing a sample for analysis. To inject a particular sample into the mobile phase for analysis, a sample needle is moved to the location of the sample. The sample is then extracted and loaded as is known in the art.

The sample needle includes a flexible portion that allows the sample needle to be moved about the sample compartment to access all sample locations. The flexible portion is coupled to a rigid portion of the sample needle. The coupling must be able to withstand the pressure (e.g., 20,000 psi) of the UPLC system. Conventional couplings can be used to couple the two portions; however, such couplings are bulky and can introduce dead volume into the flow path. The dead volume can result in carryover and can limit measurement accuracy. Although recent developments in UPLC subsystems have yielded improved overall system performance, the limitations of the coupling of the rigid and flexible portions represents a major obstacle to further improvements in high precision UPLC systems.

The present invention addresses the problems set forth above and provides additional advantages.

SUMMARY OF THE INVENTION

In one aspect, the invention features a compound sample needle for liquid chromatography. The compound sample needle includes a rigid needle, a flexible tubing and a rigid sleeve. The rigid needle has a coupling end and an internal channel for passage of a sample fluid. The coupling end has a face and a counterbore. The flexible tubing has an internal channel for passage of the sample fluid, an outer surface and a coupling end disposed in the counterbore of the rigid needle. A face on the coupling end of the flexible tubing is in contact with a base of the counterbore. The coupling ends of the rigid needle and flexible tubing are secured to each other by a weld along a circumference of the outer surface and the face of the rigid needle. The internal channel of the rigid needle portion and the internal channel of the flexible tubing are in collinear alignment at the coupling ends. The rigid sleeve is disposed over the coupling end of the rigid needle portion and the coupling end of the flexible tubing.

In another aspect, the invention features a compound sample needle for liquid chromatography. The compound sample needle includes a rigid needle, a flexible tubing and a rigid sleeve. The rigid needle has an outer surface, a coupling end having a face, and an internal channel for passage of a sample fluid. The flexible tubing has a coupling end and an internal channel for passage of the sample fluid. The coupling end of the flexible tubing has a face and a counterbore. The face of the rigid needle being in contact with a base of the counterbore. The coupling ends of the rigid needle and flexible tubing are secured to each other by a weld along a circumference of the outer surface at the face of the flexible tubing. The internal channel of the rigid needle and the internal channel of the flexible tubing are in collinear alignment at the coupling ends. The rigid sleeve is disposed over the coupling end of the rigid needle portion and the coupling end of the flexible tubing.

In yet another aspect, the invention features a compound sample needle for liquid chromatography. The compound sample needle includes a rigid needle, a flexible tubing and a rigid sleeve. The rigid needle has an internal channel for passage of a sample fluid, a coupling end with a face thereon, and an outer surface. The flexible tubing has an internal channel for passage of the sample fluid, a coupling end with a face thereon, and an outer surface. The face of the rigid needle is secured in planar contact with the face of the flexible tubing by an annular weld along a circumference of the face of the rigid needle and a circumference of the face of the flexible tubing. The internal channel of the rigid needle and the internal channel of the flexible tubing are in collinear alignment at the coupling ends. The rigid sleeve is disposed over the coupling end of the rigid needle and the coupling end of the flexible tubing.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

In brief overview, the invention relates to a compound sample needle for liquid chromatography. The compound sample needle includes a rigid needle and a flexible tubing that are secured to each other by a weld. Preferably the rigid needle has a counterbore to receive a coupling end of the flexible tubing for added structural integrity. The welded region is protected by a rigid sleeve. The compound sample needle is suitable for sampling and injection in UPLC systems where pressures can exceed 20,000 psi.

Figure 1:
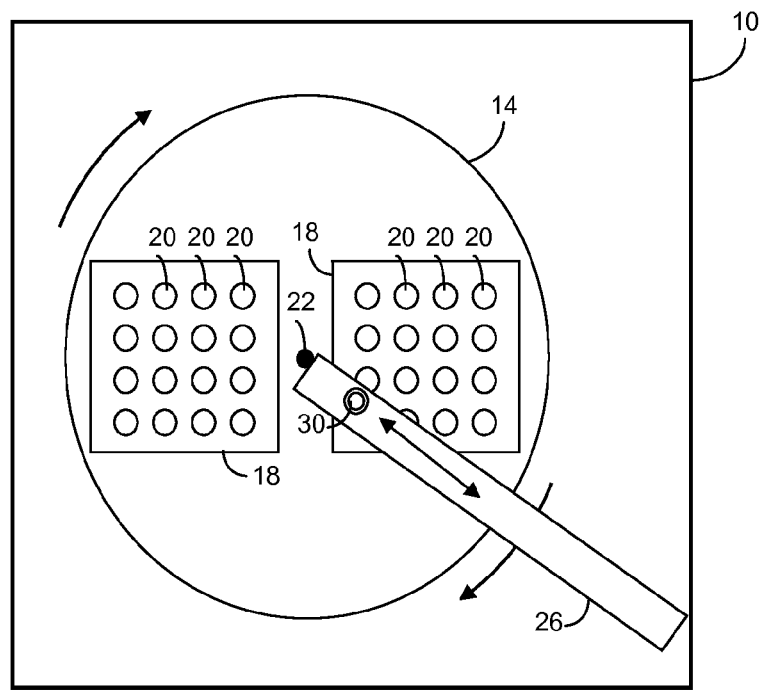
FIG. 1 illustrates a sample compartment of a UPLC system according to an embodiment of the invention.

FIG. 1 illustrates a portion of a UPLC system according to an embodiment of the invention. The system includes a sample compartment 10. As used herein, a sample compartment means an enclosure having an enclosed volume where a number of samples for chromatographic analysis are maintained in a thermally controlled environment. The illustrated sample compartment 10 includes a mounting platform 14 that holds two removable sample trays 18. Each sample tray 18 has multiple sample vials or wells that hold a sample in a fixed position 20 with respect to the other samples in the tray 18. The mounting platform 14 is coupled to a rotary drive (not shown) to enable rotation about a vertical axis 22 (i.e., normal to the plane of the figure). A needle drive 26 moves the tip 30 of a sample needle about the sample compartment 10. The rotary drive controls the angular position of each sample tray 18 with respect to the vertical axis 22. Combined control of the needle drive 26 and the rotary drive allows the tip 30 of the sample needle to be moved to the location 20 of any sample so that the sample can be extracted and injected into the mobile phase of the chromatography system.

Figure 2:
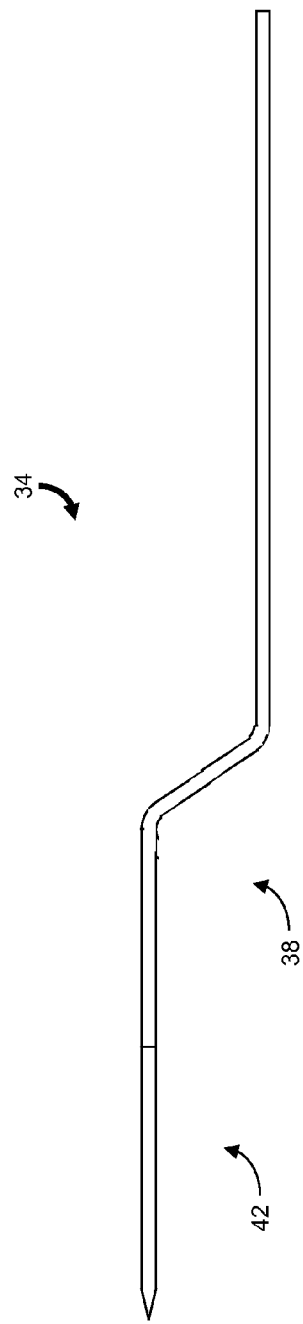
FIG. 2 illustrates a compound sample needle having a flexible tubing.

During operation of the UPLC system, the compound sample needle may be pressurized to a system pressure of 20,000 psi or greater. Referring to FIG. 2, an illustration of a compound sample needle 34 shows a flexible tubing 38 to allow motion about the sample compartment 10 for accessing the samples in the sample tray 18. The compound sample needle 34 also includes a rigid needle 42 to enable it to be inserted through a needle seal for extracting a sample from the sample tray 18 for injection into the high pressure mobile phase. The rigid needle 42 is secured to the flexible tubing 38 by a coupling union (not shown). The length of the rigid needle 42 (e.g., approximately 3 in.) is generally substantially less that the length of the flexible tubing 38 (e.g., 15-25 in.) as the flexible tubing 38 has to be sufficiently long to support a range of motion for access to all samples inside the sample compartment 10.

Figure 3:
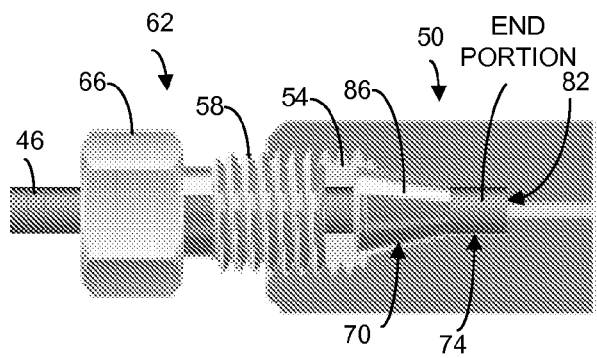
FIG. 3 is an illustration of a portion of a coupling for securing a tubing to a threaded fitting as is known in the art.

FIG. 3 is an illustration of a portion of a conventional coupling for securing a length of tubing 46 to a threaded fitting 50 as is known in the art. The threaded fitting 50 includes an inner threaded portion 54 to receive an external threaded portion 58 of a second fitting 62 having a hexagonal nut 66. The fitting 50 includes an internal cone-shaped channel 70. The narrow end of the cone-shaped channel 70 communicates with a cylindrical bore 74 having a diameter and length configured to receive an end portion of the tubing 46. The base 82 of the cylindrical bore 74 is configured to receive the end portion of the tubing 46. A ferrule 86 is used to seal the end portion to the fitting 50. The conical shape of the ferrule 86 allows it to be compressed within the cone-shaped channel 70 to form the seal.

UPLC applications require high-quality seals. If the process of connecting fittings is not performed properly or if fitting components are not matched to tight dimensional tolerances, chromatography measurements can be adversely affected. For example, if the end portion of the tubing 46 is too short, the end portion will not be seated properly on the base 82 and a dead volume will be formed. The dead volume is a region in the flow path that is not swept by the mobile phase and which can negatively impact measurements due, for example, to carryover between injections. Thus the coupling of FIG. 2 is generally not a satisfactory means for securing the rigid needle 42 to the flexible tubing 38.

Figure 4A:
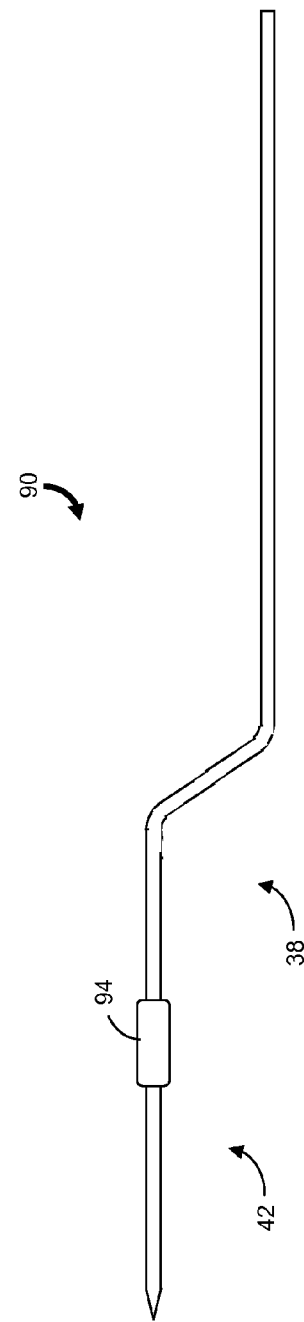
FIG. 4A shows an embodiment of a compound sample needle having a near-zero dead volume according to the invention.

FIG. 4A shows an embodiment of a compound sample needle 90 according to the invention that has near-zero dead volume. The compound sample needle 90 includes a rigid needle 42 and a flexible tubing 38 to enable the rigid needle to be movable about the sample compartment 10 and to access different locations in the sample tray 18. The compound sample needle 90 further includes a rigid sleeve 94 disposed over a coupling end of the rigid needle 42 and a coupling end of the flexible tubing 38 to protect their connection. As used herein, a coupling end means that portion of the rigid needle 42 or flexible tubing 38 that resides inside the rigid sleeve 94. In a preferred embodiment, the rigid needle 42 and flexible tubing are fabricated from 316 stainless steel although other forms of stainless steel, titanium and other materials known in the art can be used.

Figure 4B:
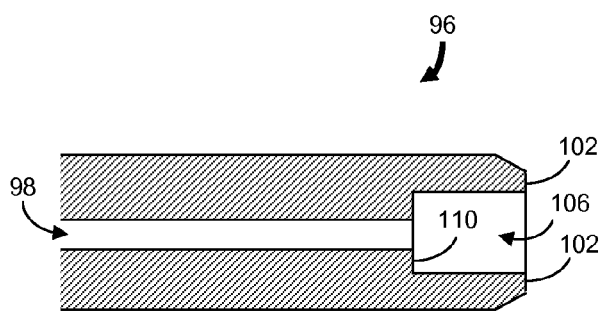
FIG. 4B shows a cross-sectional side view of a coupling end of the rigid needle in FIG. 4A.
Figure 4C:
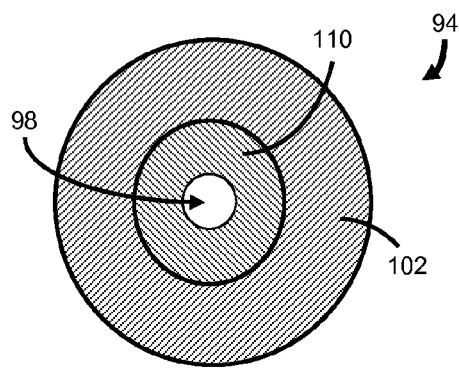
FIG. 4C shows a magnified end view of the coupling end of the rigid needle in FIG. 4A.

FIG. 4B and FIG. 4C show a cross-sectional side view and a magnified end view, respectively, of the coupling end 96 of the rigid needle 42. An internal channel 98 passes the sample for analysis during extraction from the sample tray and injection into the mobile phase. The coupling end 96 has a face 102 and a counterbore 106 that extends from the face 102 to a base 110. In one embodiment, the counterbore 106 has a diameter of 0.026 in. and the distance from the face 102 to the base is 0.040 in.

Figure 5:
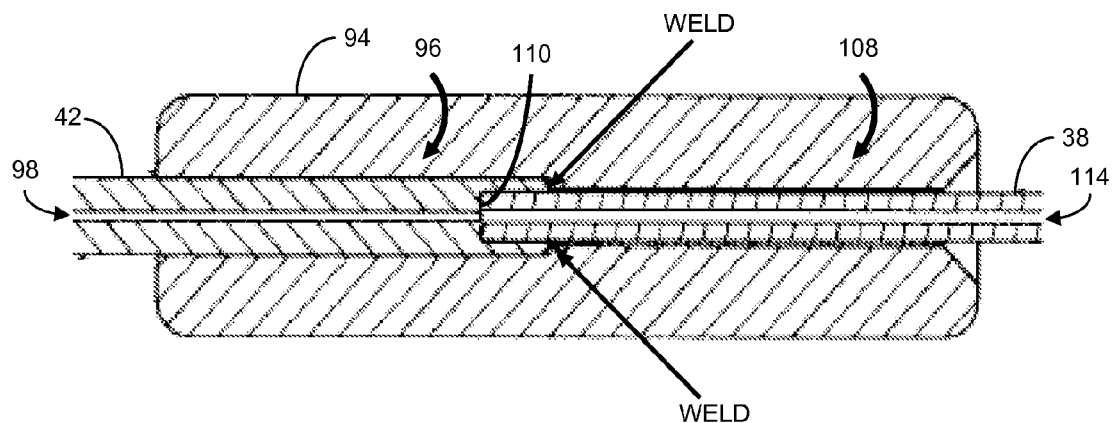
FIG. 5 is a cross-sectional view through the rigid sleeve of FIG. 4A showing the arrangement of the coupling ends of the rigid needle and the flexible tubing.

Referring to FIGS. 4B, 4C and 5, the counterbore 106 receives the coupling end 108 of the flexible tubing 38 such that a face of the flexible tubing 38 is flush with the base 110. The outer diameter of the flexible tubing 38 is closely matched to the diameter of the counterbore 106. The face 102 of the rigid needle 42 is ground to ensure a smooth surface and the surfaces of the rigid needle 42 and flexible tubing 38 in the region of their coupling ends 96 and 108 are prepared in accordance with precision welding practices. The coupling ends 96 and 108 are secured to each other using a laser welding process. In particular, a weld is formed along a circumference of the outer surface of the coupling end 108 of the flexible tubing 38 and the face 102 of the rigid needle 42. The weld has a substantially annular shape. Care is taken to maintain cleanliness during the welding process and low defect materials are used to ensure a quality weld that can withstand the high pressure requirements of UPLC chromatography.

The weld maintains the internal channel 98 of the rigid needle 42 and internal channel 114 of the flexible tubing 38 in collinear alignment. The rigid sleeve 94 provides a stiffness to the compound sample needle 90 to help protect the welded joint. The rigid sleeve 94 has a first internal diameter to closely match the outer diameter of the rigid needle 42 and a second internal diameter to closely match the outer diameter of the flexible tubing 38. In a preferred embodiment, the rigid sleeve 94 is fabricated from stainless steel.

The compound sample needle 90 can be scaled to accommodate different volumes of sample. For example, the diameters of the internal channels 98 and 114 can be altered to achieve different volumes as long as a sufficient needle thickness and tubing wall thickness are maintained.

Figure 6:
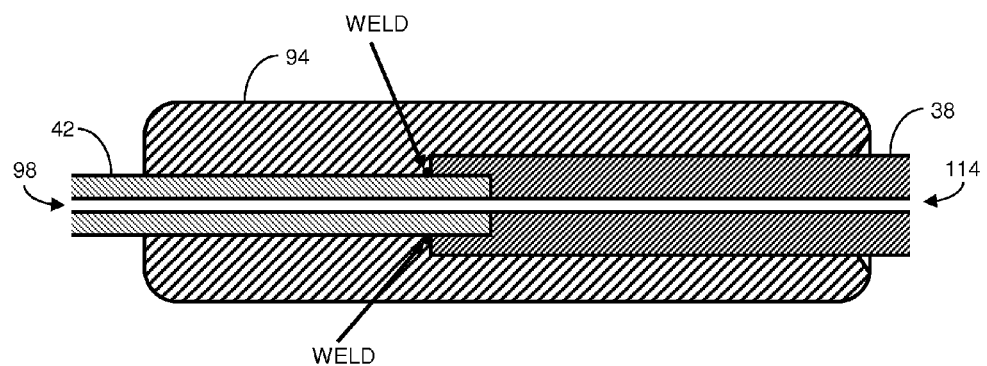
FIG. 6 is a cross-sectional view through a rigid sleeve showing the arrangement of the coupling ends of the rigid needle and the flexible tubing for another embodiment of a compound sample needle.
Figure 7:
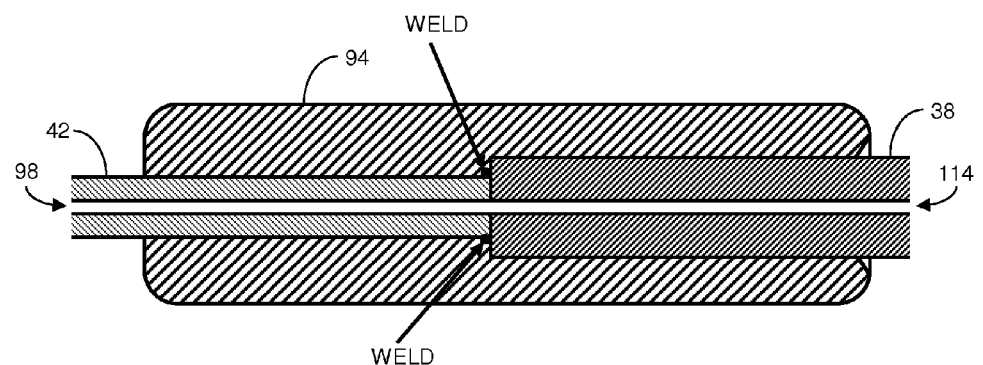
FIG. 7 is a cross-sectional view through a rigid sleeve showing the arrangement of the coupling ends of the rigid needle and the flexible tubing for another embodiment of a compound sample needle.

Although the illustrated embodiment is based on a rigid needle 42 having a counterbore at a coupling end, the invention contemplates an alternative configuration as shown in FIG. 6 in which the counterbore is formed in the coupling end of the flexible tubing 38. In this arrangement, a weld is formed along the circumference of the outer surface of the rigid needle 42 at the face of the flexible tubing 38. In another alternative configuration as shown in FIG. 7, no counterbore is used. Instead, the faces of the coupling ends are maintained in planar contact with each other by a weld along a circumference where the outer surfaces of the rigid needle 42 and flexible tubing 38 meet.

While the invention has been shown and described with reference to specific embodiments, it should be understood by those skilled in the art that various changes in form and detail may be made therein without departing from the spirit and scope of the invention as recited in the accompanying claims.

What is claimed is:

1. A compound sample needle for liquid chromatography, comprising:
    a rigid needle having a coupling end and an internal channel for passage of a sample fluid, the coupling end having a face and a counterbore;
    a flexible tubing having an internal channel for passage of the sample fluid, an outer surface and a coupling end disposed in the counterbore of the rigid needle, the coupling end of the flexible tubing having a face in contact with a base of the counterbore, the coupling ends of the rigid needle and flexible tubing being secured to each other by a weld along a circumference of the outer surface and the face of the rigid needle, the internal channel of the rigid needle portion being collinear with the internal channel of the flexible tubing at the coupling ends; and
    a rigid sleeve disposed over the coupling end of the rigid needle portion and the coupling end of the flexible tubing.

2. The compound sample needle of claim 1 wherein the rigid needle and the flexible tubing are fabricated from stainless steel.

3. The compound sample needle of claim 1 wherein the weld has a substantially annular shape.

4. A compound sample needle for liquid chromatography, comprising:
    a rigid needle having an outer surface, a coupling end having a face, and an internal channel for passage of a sample fluid;
    a flexible tubing having a coupling end and an internal channel for passage of the sample fluid, the coupling end of the flexible tubing having a face and a counterbore, the face of the rigid needle being in contact with a base of the counterbore, the coupling ends of the rigid needle and flexible tubing being secured to each other by a weld along a circumference of the outer surface at the face of the flexible tubing, the internal channel of the rigid needle being collinear with the internal channel of the flexible tubing at the coupling ends; and
    a rigid sleeve disposed over the coupling end of the rigid needle portion and the coupling end of the flexible tubing.

5. A compound sample needle for liquid chromatography, comprising:
    a rigid needle having an internal channel for passage of a sample fluid, a coupling end with a face thereon, and an outer surface;
    a flexible tubing having an internal channel for passage of the sample fluid, a coupling end with a face thereon, and an outer surface, the face of the rigid needle being secured in planar contact with the face of the flexible tubing by an annular weld along a circumference of the face of the rigid needle and a circumference of the face of the flexible tubing, the internal channel of the rigid needle being collinear with the internal channel of the flexible tubing at the coupling ends; and
    a rigid sleeve disposed over the coupling end of the rigid needle and the coupling end of the flexible tubing.

\* \* \* \* \*